United States Patent
Kita-Tokarczyk et al.

(10) Patent No.: US 11,266,587 B2
(45) Date of Patent: *Mar. 8, 2022

(54) OLIGOESTER AMMONIUM SALTS AND THEIR USE IN COMPOSITIONS FOR CONDITIONING HAIR

(71) Applicant: Clariant International Ltd., Muttenz (CH)

(72) Inventors: Katarzyna Kita-Tokarczyk, Bad Soden (DE); Hannah Benson, Bensheim (DE); Dirk Leinweber, Kelkheim (DE); Henrike Neuhoff, Hannover (DE); Steffen Romanski, Wesel (DE); Nadine Zoumpoulakis, Frankfurt (DE)

(73) Assignee: Clariant International Ltd., Muttenz (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/060,275

(22) PCT Filed: Dec. 7, 2016

(86) PCT No.: PCT/EP2016/080027
§ 371 (c)(1),
(2) Date: Jun. 7, 2018

(87) PCT Pub. No.: WO2017/097816
PCT Pub. Date: Jun. 15, 2017

(65) Prior Publication Data
US 2018/0369099 A1 Dec. 27, 2018

(30) Foreign Application Priority Data

Dec. 8, 2015 (EP) .................... 15198427
Aug. 3, 2016 (EP) .................... 16182521
Aug. 3, 2016 (EP) .................... 16182522
Aug. 23, 2016 (FR) .................... 1657858
Aug. 23, 2016 (FR) .................... 1657859
Nov. 9, 2016 (EP) .................... 16198041

(51) Int. Cl.
*A61K 8/41* (2006.01)
*A61Q 5/02* (2006.01)
*A61Q 5/12* (2006.01)
*A61K 8/34* (2006.01)
*C07C 219/06* (2006.01)
*A61K 8/81* (2006.01)
*A61K 8/65* (2006.01)
*A61K 8/67* (2006.01)

(52) U.S. Cl.
CPC .............. *A61K 8/416* (2013.01); *A61K 8/345* (2013.01); *A61K 8/41* (2013.01); *A61K 8/65* (2013.01); *A61K 8/678* (2013.01); *A61K 8/8129* (2013.01); *A61Q 5/02* (2013.01); *A61Q 5/12* (2013.01); *C07C 219/06* (2013.01)

(58) Field of Classification Search
None
See application file for complete search history.

(56) References Cited

U.S. PATENT DOCUMENTS

| | | | |
|---|---|---|---|
| 2,809,971 A | 10/1957 | Bernstein | |
| 3,236,733 A | 2/1966 | Karsten | |
| 3,753,196 A | 8/1973 | Kurtz | |
| 3,761,418 A | 9/1973 | Parran | |
| 3,958,581 A | 5/1976 | Abegg | |
| 3,962,418 A | 6/1976 | Birkofer | |
| 4,009,256 A | 2/1977 | Nowak, Jr. | |
| 4,323,683 A | 4/1982 | Bolich, Jr. | |
| 4,345,080 A | 8/1982 | Bolich, Jr. | |
| 4,379,753 A | 4/1983 | Bolich, Jr. | |
| 4,470,982 A | 9/1984 | Winkler | |
| 4,529,773 A | 7/1985 | Witiak | |
| 5,194,639 A | 3/1993 | Connor | |
| 5,880,299 A | 3/1999 | Ponsati Obiols | |
| 5,888,489 A | 3/1999 | Von Mallek | |
| 6,300,307 B1 | 10/2001 | Bermejo | |
| 6,432,895 B1 * | 8/2002 | Bigorra | ......... A61K 8/416 510/119 |

(Continued)

FOREIGN PATENT DOCUMENTS

| | | |
|---|---|---|
| BR | 112018010272 | 11/2018 |
| BR | 112018010433 | 11/2018 |

(Continued)

OTHER PUBLICATIONS

Bigorra etal. DE 19743687, English machine translation obtained on Jul. 6, 2020. (Year: 1998).
CTFA Cosmetic Ingredient Handbook, Second Edition, 1992, 2 pages.
International Search Report for PCT/EP2016/080027, dated Feb. 8, 2017, 3 pages.
International Search Report for PCT/EP2016/080031, dated Feb. 8, 2017, 4 pages.

(Continued)

*Primary Examiner* — H. Sarah Park
(74) *Attorney, Agent, or Firm* — Tod A. Waldrop

(57) ABSTRACT

The invention relates inter alia to cosmetic compositions comprising an oligoester ammonium salt (OAS) and a cosmetically component (F), where the OAS is obtained by:

(i) heating a mixture of the following components (a) to (d) under continuously removing of reaction water: (a) a certain a diethanolamine compound; (b) a certain dicarboxylic acid; (c) a certain organic triol; and a monocarboxylic acid of formula $R^1$—COOH (d), wherein $R^1$ is linear or branched $C_{12}$-$C_{24}$-alkyl;

(ii) reacting the oligoester of step (i) with a quarternization agent.

11 Claims, No Drawings

(56) References Cited

U.S. PATENT DOCUMENTS

| | | | |
|---|---|---|---|
| 6,737,392 B1 | 5/2004 | Keys | |
| 7,101,538 B1 * | 9/2006 | Tang | A61K 8/046 |
| | | | 424/401 |
| 7,786,319 B2 | 8/2010 | Bigorra Llosas | |
| 2003/0013627 A1 | 1/2003 | Bermejo Oses | |
| 2003/0130162 A1 | 7/2003 | Llosas | |
| 2005/0288198 A1 | 12/2005 | Pereira | |
| 2006/0258556 A1 | 11/2006 | Holderbaum | |
| 2008/0214776 A1 * | 9/2008 | Bigorra Llosas | C07C 219/06 |
| | | | 528/335 |
| 2018/0353410 A1 | 12/2018 | Kita-Tokarczyk | |
| 2018/0360714 A1 | 12/2018 | Kita-Tokarczyk | |
| 2018/0369099 A1 | 12/2018 | Kita-Tokarczyk | |

FOREIGN PATENT DOCUMENTS

| | | |
|---|---|---|
| BR | 112018010358 | 12/2018 |
| CN | 1425363 | 6/2003 |
| CN | 108391417 | 8/2018 |
| CN | 108391418 | 8/2018 |
| CN | 108391419 | 8/2018 |
| DE | 19642038 | 12/1997 |
| DE | 19710155 | 9/1998 |
| DE | 19715835 | 11/1998 |
| DE | 19743687 | 11/1998 |
| DE | 202017101868 | 7/2017 |
| EP | 0116838 | 8/1984 |
| EP | 0530974 | 3/1993 |
| EP | 0550637 | 7/1993 |
| EP | 1136471 | 9/2001 |
| EP | 1160238 | 12/2001 |
| EP | 3386472 | 10/2018 |
| EP | 3386473 | 10/2018 |
| EP | 3386474 | 10/2018 |
| FR | 3038834 | 1/2017 |
| FR | 3038835 | 1/2017 |
| JP | S59139312 | 8/1984 |
| JP | 2001512538 | 8/2001 |
| JP | 2001335545 | 12/2001 |
| JP | 2003519294 | 6/2003 |
| JP | 2014167190 | 9/2014 |
| JP | 2018536672 | 12/2018 |
| JP | 2018536674 | 12/2018 |
| JP | 2018536675 | 12/2018 |
| KR | 100992594 | 11/2010 |
| WO | 9206154 | 4/1992 |
| WO | 9522311 | 8/1995 |
| WO | 9631188 | 10/1996 |
| WO | 9849132 | 11/1998 |
| WO | 03063790 | 8/2003 |
| WO | 2013178700 | 12/2013 |
| WO | 2015091308 | 6/2015 |
| WO | 2015110269 | 7/2015 |
| WO | 2017097816 | 6/2017 |
| WO | 2017097817 | 6/2017 |
| WO | 2017097819 | 6/2017 |

OTHER PUBLICATIONS

International Search Report for PCT/EP2016/080033, dated Feb. 8, 2017, 4 pages.
US Pharmacopeia NF, "Nitrogen Determination", 2013, 1 page.

* cited by examiner

OLIGOESTER AMMONIUM SALTS AND THEIR USE IN COMPOSITIONS FOR CONDITIONING HAIR

The present invention relates to cosmetic compositions, in particular hair conditioner compositions, comprising at least one oligoester ammonium salt, methods of preparing the cosmetic compositions, their use as well as methods of treating the hair.

Methods for cleaning and conditioning of hair are known for centuries. Frequently, the cleaning methods require an alkaline agent, such as soap. The interaction of this agent with hair results in weakening its mechanical properties and increases the porosity of hair fibers. Many known shampooing components result in dry hair that is damaged. Furthermore, the color of hair often fades with time due to washing and upon exposure to environmental factors such as sun and pollution. This can lead to dull appearance of the hair and results in more frequent washing than required. Frequent washing of hair may result in more damaged and less conditioned hair.

In order to improve the condition of hair and to keep a natural look of the hair over a longer period of time, improved hair care regimens and conditioning compositions are required. In particular the gloss (shine) of the hair and force needed for combing and detangling the hair are important characteristics.

Natural oils have been used for centuries to condition human hair. Essential oils (e.g. tea tree oil) and carrier oils (e.g. jojoba oil) have been used. Human hair contains about 97% of the protein keratin, which needs to be protected to preserve the strength and natural look.

The surface of keratin contains negatively charged amino acids. For this reason, hair conditioners can contain cationic components (e.g. surfactants) which are not washed out completely. The hydrophilic ends of the cationic components can bind to the keratin, whereas the hydrophobic ends of the molecules protect the hair surface.

Modern hair conditioner compositions are often intended to soften the hair, to improve the gloss of hair and to avoid a greasy look of the hair. Fatty alcohols, silicone derivatives and quaternary ammonium compounds were used for hair conditioner compositions, which coat the cuticle of the hair.

Hair conditioner compositions can be used together with shampoo compositions or separately. Hair conditioner compositions comprise generally one or more of the following types of ingredients (components):

acidity regulators, which maintain the conditioner's pH at about 3 to 5;

antistatic agents;

glossers, light-reflecting polymer components binding to the hair surface, such as silicones, e.g., dimethicone or cyclomethicone;

lubricants, such as fatty alcohols or pro-vitamins, such as panthenol;

moisturizers, which hold moisture in the hair and often contain humectants;

oils (e.g. natural oils) for the hair to become soft and pliable;

preservatives, to avoid microorganisms-growth in the composition;

sequestrants, for improving the function of the composition in hard water;

strengtheners, often containing hydrolyzed protein, to penetrate the hair and reinforce the structure, e.g. through polymer crosslinking;

sun protectors against protein degradation and color loss, e.g. benzophenone; and surfactants, such as non-ionic surfactants, or ionic surfactants.

Among many market trends, not only in cosmetics, it has been seen that ecological (also called green, natural or eco-friendly) products attract more consumers than before. To provide such products, ingredients are sought with good biodegradability, low irritation potential, non-allergenic, and with little impact on the environment. Often, such products are based on the (poly)ester chemistry, which can hydrolyze and degrade in aquatic environments. Esterquats are available from German manufacturers, such as Evonik or BASF.

DE-A 19710155 discloses a microemulsion comprising polyester ammonium salts of general formula (H),

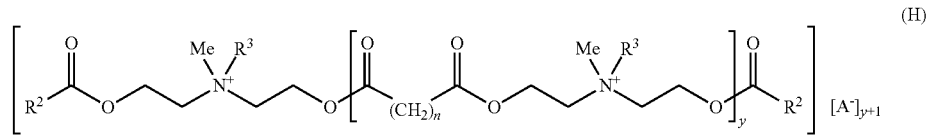

wherein
$R^2$ is $C_{11}$-$C_{21}$-alkyl,
$R^3$ is $C_1$-$C_4$-alkyl or hydroxyethyl,
n from 1 to 7,
y is either 0 or 1, and
[$A^-$] is halogen or methylsulfate.

Therein a conditioning agent is proposed and the application of a micro-emulsion in hair conditioning is said to provide typical conditioning benefits, such as improved smoothness, softness and ease of combing wet hair.

DE-C 19743687 discloses a detergent composition comprising ester ammonium salts of general formula (K),

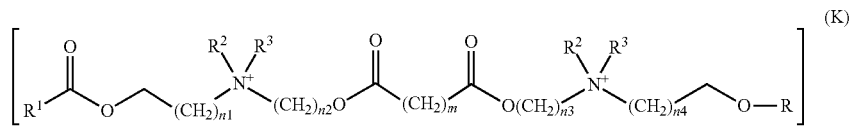

wherein
$R^1$ is $C_5$-$C_{21}$-alkyl;
$R^2$ is $C_1$-$C_4$-alkyl;
$R^3$ is selected from $C_1$-$C_4$-alkyl or hydroxy-($C_1$-$C_4$-alkyl);

m is from 1 to 10; and n1, n2, n3, n4 are from 0 to 4.

Therein it is further disclosed that the use of the composition in hair conditioning results in electrostatic charge reduction, ease of combing wet and dry hair, and improved softness. All of these effects are all typical for conditioning agents.

Hence, both the ester ammonium salts (H) and (K) are said to produce effects typical for conditioning agents. Nothing is to be found about other properties of this kind of compounds. U.S. Pat. No. 7,101,538 describes a topical composition for skin, hair and nail treatment containing a polyester amine component. EP-A 1160238 discloses a process for preparing polyester quats. The application WO 2003/063790 describes various types of oligoester components for cosmetic applications.

Shine, gloss and surface smoothening are all desirable attributes in cosmetic compositions and preparations for personal care. For example, shine and gloss are highly desired attributes in nail color and hair care preparations. Surface smoothening is important in shampoos, hair conditioners and other hair treatment preparations and can provide superior wet and dry hair combing. However, such attributes can often only be attained by combining several different ingredients in the cosmetic compositions. Thus, there is still a great need in personal care for new compositions and/or components that deliver multiple effects at the same time, such as several of the aforementioned attributes and benefits. In particular there is a great need for providing such compositions and/or components that provide excellent performance as a conditioner and a wide variety of cosmetic benefits simultaneously.

It is an objective of the present invention to provide cosmetic compositions, in particular hair conditioner compositions, comprising an ingredient that delivers at the same time multiple effects. The composition and its components can be prepared easily and provide or enhance several of the following benefits: hair detangling, improved wet and dry combing, shine (gloss) such as hair gloss without the need for silicone, conditioning, (hair) surface smoothening, hair repair, water resistance, film-forming properties, static charge reduction, anti-frizz, volume, thickening and surfactant activity.

In a first aspect, the problems mentioned herein are solved by a cosmetic composition, in particular hair conditioner composition, comprising at least one oligoester ammonium salt (OAS) and at least one further cosmetically acceptable component (F), whereby the at least one oligoester ammonium salt (OAS) is obtainable by the following steps:

(i) heating a mixture of the following components (a) to (d) under continuously removing of reaction water:
  0.5 to 3.0 molar equivalents, often 0.75 to 3.0 molar equivalents, of a diethanolamine compound represented by the formula (a)

(a)

wherein $R^3$ is a linear or branched $C_1$-$C_6$-alkyl, preferably linear or branched $C_1$-$C_4$-alkyl, more preferably methyl or ethyl;

0.5 to 1.5 molar equivalents of a dicarboxylic acid represented by the formula (b)

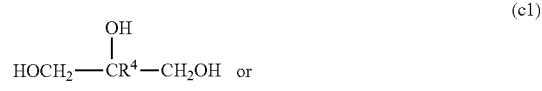

(b)

wherein $R^2$ is a linear or branched $C_1$-$C_{10}$-alkylene or a linear or branched $C_2$-$C_{10}$-alkenylene, preferably $C_2$-$C_8$-alkylen, more preferably $C_4$-alkylene;

0.5 to 1.5 molar equivalents of an organic triol represented by the formula (c1) or (c2)

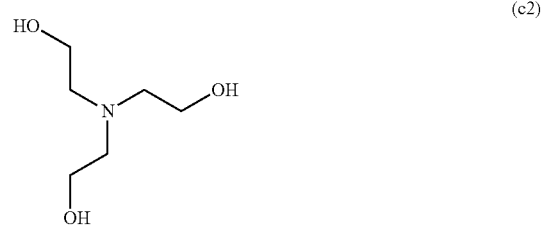

(c1)

(c2)

wherein $R^4$ is hydrogen or linear or branched $C_1$-$C_4$-alkyl or hydroxyl-$C_1$-$C_4$-alkyl, preferably hydrogen, methyl or ethyl, more preferably hydrogen;

1.0 molar equivalent of a monocarboxylic acid represented by formula (d)

$R^1$—COOH                                            (d)

wherein $R^1$ is linear or branched $C_{12}$-$C_{24}$-alkyl or linear or branched $C_{12}$-$C_{24}$-alkenyl, preferably linear or branched $C_{12}$-$C_{22}$-alkyl or linear or branched $C_{12}$-$C_{22}$-alkenyl, more preferably $C_{20}$-$C_{22}$-alkyl;

(ii) reacting the oligoester product of step (i) with a quaternization agent (e), in particular from the group of dimethyl sulfate, diethyl sulfate and alkyl halides;

(iii) optionally removing and purifying the at least one oligoester ammonium salt.

The OAS (and the cosmetic composition) is preferably prepared wherein the di-ethanolamine component (a) wherein $R^3$ is methyl.

The OAS (and cosmetic composition) is preferably prepared wherein the dicarboxylic acid (b) is selected from the group consisting of adipic acid, glutaric acid, succinic acid, sebacid acid, itaconic acid, maleic acid, and combinations thereof.

The OAS (and cosmetic composition) is preferably prepared wherein the organic triol (c) is selected from the group consisting of glycerol, triethanolamine, and combinations thereof.

The OAS (and cosmetic composition) is preferably prepared by choosing the carboxylic acid (d) selected from the group consisting of behenic acid, oleic acid, coconut fatty acid, linoleic acid, and combinations thereof.

The OAS (and cosmetic composition) is preferably prepared by choosing the components (a), (b), (c) and (d) in the following molar ratios: from 0.5-3.0 (a), from 0.5-1.5 (b), from 0.5-1.5 (c) and 1 (d). The component (a) can also preferably be used in a molar ratio of 0.75-3.0.

The OAS (and cosmetic composition) is preferably prepared by choosing the molar ratio of the components (a), (b), (c) and (d) such that the molar equivalents of hydroxyl functions are in excess of the molar equivalents of the acid functions.

The OAS (and cosmetic composition) is preferably prepared by choosing a process, whereby first heating the mixture of components (a), (b), (c) and (d) in step (i) to a temperature from 80 to 220° C., preferably from 150 to 210° C., more preferably from 160 to 200° C. is used, and in step (ii) subsequent reaction of the obtained oligoester product occurs with a quaternization agent (e), preferably selected from the group consisting of dimethyl sulfate, diethyl sulfate, methylchloride, ethylchloride, butylchloride, and combinations thereof.

The cosmetic composition is preferably prepared wherein the oligoester ammonium salt (OAS) having a molecular mass Mn (number average) of from 500 to 4000 g/mol, preferably from 600 to 4000 g/mol, more preferably from 650 to 2000 g/mol, even more preferably from 665 to 1800 g/mol.

In a particularly preferred embodiment of the first aspect, the components (a) to (c) are: methyl diethanol amine (component (a)), behenic acid (component (d)), adipic acid or sebacic acid (component (b)), and glycerol (component (c)), respectively.

In a second aspect, the invention also relates to a cosmetic composition, in particular hair conditioner composition, comprising at least one oligoester ammonium salt (OAS) of formula (I) and at least one further cosmetically acceptable component (F),

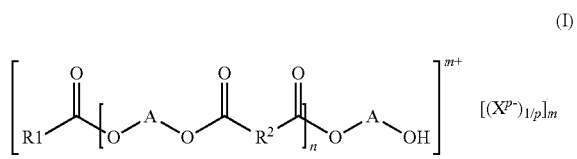

(I)

wherein:
$R^1$ is a linear or branched $C_{12}$-$C_{24}$-alkyl or linear or branched $C_{12}$-$C_{24}$-alkenyl group, preferably a linear or branched $C_{12}$-$C_{22}$-alkyl or linear or branched $C_{12}$-$C_{22}$-alkenyl group, more preferably a linear or branched $C_{20}$-$C_{22}$-alkyl group;
$R^2$ is a linear or branched $C_1$-$C_8$-alkylene or linear or branched $C_2$-$C_8$-alkenylene group;
A is, at least once, independently selected from compounds conforming to:
($C_1$-$C_6$-alkylene)-$CR^5R^6$—($C_1$-$C_6$-alkylene), preferably conforming to ($C_1$-$C_4$-alkylene)-$CR^5R^6$—($C_1$-$C_4$-alkylene),
wherein $R^5$ and $R^6$ are each independently selected from the group consisting of H, OH, $C_1$-$C_6$-alkyl, and hydroxy-$C_1$-$C_6$-alkyl;
and is, at least once, independently selected from quaternary ammonium compounds of the formula (II)

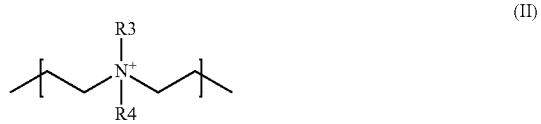

(II)

wherein $R^3$, $R^4$ are each independently linear or branched $C_1$-$C_6$-alkyl or linear or branched hydroxy-$C_1$-$C_6$-alkyl groups;
n is an integer from 1 to 30, preferably from 1 to 10; and
m is an integer from 1 to 31, describing the charge, preferably m is an integer from 1 to 10;
$[(X^{p-})_{1/p}]$ is a counter-ion selected from the group consisting of monovalent anions having the formula $[X^-]$, divalent anions having the formula $[(X^{2-})_{0.5}]$, and trivalent anions having the formula $[(X^{3-})_{1/3}]$.

The phrase "A is, at least once, independently selected from" means that the compound conforming to formula (I) must contain, at position A, a compound conforming to the requirements thereafter described. Indeed, since n is an integer from 1 to 30, not all of the repeating units described in the square brackets for n need be exactly the same chemically. Hence, where n is 3, then A described in the square brackets for n could be three different chemical groups or the same chemical group. The phrase "A is, at least once, independently selected from" means that the compound conforming to formula (I) must contain, at position A, at least once a compound conforming to the requirements thereafter described—where n is 3, then A could be said compound for all repeating units, or only for one occurrence of A—the minimum is a least once.

In at least one embodiment of the cosmetic composition, in formula (I) the group A conforms to ($C_1$-$C_4$-alkylene)-$CR^5R^6$—($C_1$-$C_4$-alkylene), wherein $R^5$ and $R^6$ are each independently selected from the group consisting of H, OH, $C_1$-$C_2$-alkyl, and hydroxy-methyl.

In at least one embodiment the cosmetic composition relates to wherein in formula (I) the compounds conforming to ($C_1$-$C_6$-alkylene)-$CR^5R^6$—($C_1$-$C_6$-alkylene) are selected from the group consisting of:
—$CH_2$—CH[OH]—$CH_2$—,
—$CH_2$—CH[$CH_2OH$]—$CH_2$—,
—$CH_2$—C[$CH_3$][$CH_2OH$]—$CH_2$—,
—$CH_2$—C[$CH_2CH_3$][$CH_2OH$]—$CH_2$—, and
—$CH_2$—C[$CH_2OH$]$_2$—$CH_2$—.

In at least one embodiment of the cosmetic composition, wherein in formula (I), the group A is, at least once, independently selected from compounds conforming to: ($C_1$-$C_4$-alkylene)-$NR^7$—($C_1$-$C_4$-alkylene), wherein $R^7$ is hydroxy-$C_1$-$C_2$-alkyl.

In at least one embodiment of the cosmetic composition, wherein in formula (I) the counter ion of the formula $[(X^{p-})_{1/p}]$ is selected from the group consisting of Cl$^-$ (chloride), Br$^-$ (bromide), $MeSO_4^-$ (methyl sulfate), $EtSO_4^-$ (ethyl sulfate), $HCO_2^-$ (formate), citrate, acetate, nitrate, $[(CO_3^{2-})_{0.5}]$ (carbonate), $[(SO_4^{2-})_{0.5}]$ (sulfate), $[(PO_4^{3-})_{1/3}]$ (phosphate), and combinations thereof.

In at least one embodiment the cosmetic composition, comprises from 0.01 to 20% by weight of one or more oligoester ammonium salts (OAS) and further comprises at least 0.5% by weight of one or more further components (F) selected from the group consisting of acidity regulators, glossers, lubricants, and further surfactants.

In at least one embodiment the composition preferably comprises from 0.01 to 20% by weight of one or more OAS and at least 0.5% by weight of further surfactant(s), preferably cetrimonium chloride (CTAC).

A third aspect relates to the use of an oligoester ammonium salt (OAS) obtained by a process as defined above, or of an oligoester ammonium salt (OAS) of formula (I) as a surfactant in cosmetic compositions, preferably in hair conditioner compositions.

A fourth aspect relates to a method of preparing a cosmetic composition, in particular hair conditioner composition, comprising the step of preparing one or more oligoester ammonium salts (OAS) as described above, and mixing the OAS with one or more further components (F) and water.

A fifth aspect relates to a method of treating hair, comprising:
a) applying the hair conditioner composition according to the first aspect or the second aspect onto wet hair and then
b) removing the conditioner composition from the hair.

At least one embodiment of the fifth aspect relates to a method of treating hair, comprising:
(a) applying a shampoo composition onto the hair; and then
(b) washing the hair with the shampoo composition; and then
(c) removing the shampoo composition from the hair; and then
(d) applying the hair conditioner composition onto wet hair, and then removing the conditioner composition from the hair.

In the context of the present invention, the expression "$C_1$-$C_{24}$-alkyl" includes all kind of acyclic and cyclic alkyl groups with 1 to 24 carbon atoms. In at least one embodiment, the compounds conforming to $C_1$-$C_{24}$-alkyl are selected from the group consisting of methyl, ethyl, n-propyl, iso-propyl, n-butyl, sec-butyl, iso-butyl, tert-butyl, n-pentyl, 1-methylbutyl, 2-methylbutyl, 3-methylbutyl, 1,1-dimethylpropyl, 2,2-dimethylpropyl, 1,2-dimethylpropyl, 1-ethylpropyl, n-hexyl, 1-methylpentyl, 2-methylpentyl, 3-methylpentyl, 4-methylpentyl, 1,1,-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1-ethyl-1-methyl-propyl, 1-ethyl-2-methylpropyl, 2-ethyl-1-methyl-propyl and 2-ethyl-2-methylpropyl, n-heptyl, 5-methylhexyl, 2-ethyl-3-methylbutyl, n-octyl, 5-methyl-heptyl, 4,4-dimethylhexyl, 3-ethylhexyl, 2-ethyl-3-methyl pentyl, nonyl, decyl, undecyl, dodecyl, tridecyl, tetradecyl, pentadecyl, hexadecyl, heptadecyl, octadecyl, nonadecyl, eicosanyl, heneicosanyl, docosanyl, tricosanyl, tetracosanyl, as well as cyclopropyl, cyclobutyl, cyclopentyl, 1-metylcyclobutyl, 2-methylcyclobutyl, 3-methylcyclo-butyl, cyclohexyl, 1-methyl-cyclopentyl, 2-methylcyclopentyl, 3-methylcyclopentyl, 1,2-dimethylcyclobutyl, 1,3-dimethylcyclobutyl, 2,2-dimethylcyclobutyl, 2,3-dimethylcyclobutyl and 3,3-dimethylcyclobutyl, cyclo-decyl, decalinyl, and mixtures thereof.

In the context of the present invention, the expression "$C_2$-$C_{24}$-alkenyl" includes all kind of acyclic and cyclic hydrocarbon groups with 2 to 24 carbon atoms and one or more C—C double bonds. In at least one embodiment, the compounds conforming to $C_2$-$C_{24}$-alkenyl are selected from the group consisting of vinyl, prop-1-enyl, prop-2-enyl, methallyl, 1-methylallyl, homoallyl, but-2-enyl, pent-1-enyl, pent-2-enyl, pent-3-enyl, 1-methylbut-1-enyl, 2-methylbut-1-enyl, 3-methylbut-1-enyl, 1-methylbut-2-enyl, 2-methylbut-2-enyl, 3-methylbut-2-enyl, 1-methyl-but-3-enyl, 2-methylbut-3-enyl, 3-methylbut-3-enyl, 1-ethylprop-1-enyl, 1-ethyl-prop-2-enyl, hex-1-enyl, hex-2-enyl, hex-3-enyl, hex-4-enyl, hex-5-enyl, 1-methylpent-1-enyl, 2-methylpent-1-enyl, 3-methylpent-1-enyl, 4-methylpent-1-enyl, 1-methylpent-2-enyl, 2-methylpent-2-enyl, 3-methylpent-2-enyl, 4-methylpent-2-enyl, 1-methylpent-3-enyl, 2-methylpent-3-enyl, 3-methylpent-3-enyl, 4-methylpent-3-enyl, 1-methylpent-4-enyl, 2-methylpent-4-enyl, 3-methylpent-4-enyl, 4-methylpent-4-enyl, 1,2-dimethylbut-1-enyl, 1,3-dimethylbut-1-enyl, 3,3-dimethylbut-1-enyl, 1,1-dimethylbut-2-enyl, 1,2-dimethylbut-2-enyl, 1,3-dimethylbut-2-enyl, 2,3-dimethylbut-2-enyl, 1,1-dimethylbut-3-enyl, 1,2-dimethylbut-3-enyl, 1,3-dimethylbut-3-enyl, 2,2-dimethylbut-3-enyl and 2,3-dimethylbut-3-enyl, heptenyl, octenyl, nonenyl, decenyl, undecenyl, dodecenyl, tridecenyl, tetradecenyl, pentadecencyl, hexadecenyl, heptadecenyl, octadecenyl, nonadecenyl, eicosenyl, heneicosenyl, docosenyl, tricosenyl, tetracosenyl, and cyclobut-1-enyl, cyclobut-2-enyl, cyclopent-1-enyl, cyclopent-2-enyl, cyclopent-3-enyl, cyclohex-1-enyl, cyclohex-2-enyl, cyclohex-3-enyl, cyclodecenyl, and mixtures thereof.

Within the context of the present invention the expression "$C_1$-$C_{10}$-alkylene" includes all kind of acyclic, saturated hydrocarbon units having the formula $C_mH_{2m}$, all kind of monocyclic, saturated hydrocarbon units having the formula $C_mH_{2m-2}$ and all kind of bicyclic, saturated hydrocarbon units having the formula $C_mH_{2m-4}$, wherein m in said formulae is an integer selected from 1 to 10, where possible. In at least one embodiment, the compounds conforming to $C_1$-$C_{10}$-alkylene are selected from the group consisting of: methylene, ethylene, n-propylene, 1-methylethylene, 2-methylethylene, butylene, 1-methylpropylene, butylene, 2-methyl-propylene, 3-methylproylene, 1,1-dimethylethylene, 1,2-dimethylethylene, pentylene, 1-methylbutylene, 2-methylbutylene, 3-methylbutylene, 1,1-dimethylpropylene, 2,2-dimethyl-propylene, 1,2-dimethylpropylene, 1-ethylpropylene, hexylene, 1-methylpentylene, 2-methylpentylene, 3-methylpentylene, 4-methylpentylene, 1,1,-dimethylbutylene, 1,2-dimethylbutylene, 1,3-dimethylbutylene, 2,2-dimethylbutylene, 2,3-dimethylbutylene, 3,3-dimethylbutylene, 1-ethylbutylene, 2-ethylbutylene, 1-ethyl-1-methyl-propylene, 1-ethyl-2-methylpropylene, 2-ethyl-1-methyl-propylene, 2-ethyl-2-methyl-propylene, heptylene, 5-methylhexylene, 2-ethyl-3-methylbutylene, octylene, 5-methyl-heptylene, 4,4-dimethyl-hexylene, 3-ethylhexylene, 2-ethyl-3-methylpentylene, nonylene and decylene as well as 1,3-cyclopentylene, 1,3-cyclohexylene, decalinylene, and mixtures thereof.

In the context of the present invention, the expression "$C_2$-$C_{10}$-alkenylene" includes all kind of acyclic, mono-unsaturated hydrocarbon units having the formula $C_mH_{2m-2}$, all kind of acyclic di- and poly-unsaturated hydrocarbon units having the formulae $C_mH_{2m-4}$, $C_mH_{2m-6}$ etc., as well as cyclic, mono- and di-unsaturated hydrocarbon units having the formulae $C_mH_{2m-4}$, $C_mH_{2m-6}$ etc., wherein m in said formulae is an integer selected from 2 to 10, where possible. In at least one embodiment, the compounds conforming to $C_2$-$C_{10}$-alkenylene are selected from the group consisting of: ethenylene, prop-1-enylene, prop-2-enylene, but-1-enylene, but-2-enylene, but-3-enylene, pent-1-enylene, pent-2-enylene, pent-3-enylene, pent-4-enylene, pent-5-enylene, 1-methylbut-1-enylene, 1-methylbut-2-enylene, 1-methylbut-3-enylene, hex-1-enylene, hex-2-enylene, hex-3-enylene, hept-1-enylene, hept-2-enylene, hept-3-enylene, oct-1-enylene, oct-2-enylene, oct-3-enylene, oct-4-enylene, non-1-enylene, non-2-enylene, non-3-enylene, non-4-enylene, dec-1-enylene, dec-2-enylene, hexa-1,3-dienylene, hexa-2,4-dienylene, hexa-1,3,5-trienylene, 1,3-cyclopent-4-enylene, 1,3-cylohex-4-enylene, and mixtures thereof.

Preferably, each $R^1$ in the oligoester ammonium salt of formula (I) is independently selected from compounds being linear or branched $C_{12}$-$C_{24}$-alkyl groups. More preferably, each $R^1$ is independently selected from compounds being linear or branched $C_{16}$-$C_{22}$-alkyl groups. In a more preferred embodiment of the present invention, $R^1$ is $C_{17}$-alkyl, which can be, for example, the alkyl part of an isooctadecanoic acid, even more preferably the alkyl part of isostearic acid.

In a preferred embodiment, $R^1$ is linear or branched $C_{20}$-$C_{22}$-alkyl. In another preferred embodiment, $R^1$ is $C_{21}$-alkyl, which can be the alkyl part of behenic acid.

Preferably, —$R^2$— in the oligoester ammonium salt is independently selected from the compounds being linear —($C_2$-$C_8$-alkylene)— groups. More preferably, the compounds being "linear —($C_2$-$C_6$-alkylene)—" groups are selected from the group consisting of —$CH_2$—$CH_2$— (ethylene), —$CH_2$—$CH_2$—$CH_2$— (propylene), —$CH_2$—$CH_2$—$CH_2$—$CH_2$— (butylene), —$CH_2$—$CH_2$—$CH_2$—$CH_2$—$CH_2$— (pentylene), —$CH_2$—$CH_2$—$CH_2$—$CH_2$—$CH_2$—$CH_2$— (hexylene), and mixtures thereof. Particularly preferred for —$R^2$— is —$CH_2$—$CH_2$—$CH_2$—$CH_2$—, or —$CH_2$—$CH_2$—$CH_2$—$CH_2$—$CH_2$—$CH_2$—.

In at least one embodiment of the present invention, in the oligoester ammonium salt —$R^3$ is —($C_1$-$C_4$-alkyl).

In the oligoester ammonium salt, $R^4$ is preferably selected from hydrogen, methyl or ethyl. More preferably, $R^4$ is methyl.

In the context of the present invention, the letter "n" in general formula (I) defines the average number of repeating units of the oligoester ammonium salts. The number n is preferably an integer of from 1 to 30, more preferably from 1 to 10.

In the oligoester ammonium salt of general formula (I), the counter ion $[(X^{p-})_{1/p}]$ of the (m) charged oligoester ammonium cation is preferably selected from the group consisting of: $Cl^-$ (chloride), $Br^-$ (bromide), $MeSO_4^-$ (methyl-sulfate), $EtSO_4^-$ (ethyl sulfate), $HCO_2^-$ (formate), citrate, acetate, nitrate, $[(CO_3^{2-})_{0.5}]$ (carbonate), $[(SO_4^{2-})_{0.5}]$ (sulfate), $[(PO_4^{3-})_{1/3}]$ (phosphate), and combinations thereof.

The cosmetic composition comprises also one or more further components (F), which can be in an amount of at least 0.5% by weight, such as 0.5 to 20% by weight of the cosmetic composition. Preferably, the component (F) is selected from the group consisting of: acidity regulators, colorants, further conditioning agents, emulsifiers, film formers, fragrances, glossers, humectants, lubricants, moisturizers, pigments, preservatives, skin penetration enhancers, stabilizers, further surfactants, thickeners, and viscosity modifiers. More preferably, the component (F) is selected from the group consisting of acidity regulators, glossers, lubricants, and further surfactants.

Suitable lubricants are, for example, fatty alcohol components having 6 to 18 carbon atoms. The further surfactants may, for example, be chosen from non-polymeric, cationic quaternary ammonium compounds, in particular cetrimonium chloride (CTAC).

Suitable classical cationic conditioning agents include cationic quaternary ammonium salts. Examples of such quaternary ammonium salts include benzyl triethyl ammonium chloride, cetyl trimethylammonium chloride (cetrimonium chloride, CTAC), behentrimonium chloride (BTAC) and cetylpyridinium chloride.

As cationic components, a variety of further cationic polymers are suitable, including quaternized cellulose ethers, copolymers of vinylpyrrolidone, acrylic polymers, including homopolymers or copolymers of dimethyldiallylammonium chloride and acrylamide. Also suitable are various types of homo- or copolymers derived from acrylic or methacrylic acid, acrylamide, methylacrylamide, diacetone-acrylamide.

For the method of treating hair according to the invention, a shampoo composition can be used, but the conditioner composition can also be used without using a shampoo composition.

In at least one embodiment, shampoo compositions comprise from 1 to 99%, preferably from 5 to 95%, more preferably from 10 to 90% by weight of the total composition of water, and from 0.1 to 99%, preferably from 1 to 95%, more preferably from 5 to 90%, often 5 to 25% by weight of the total composition of a cleansing surfactant. Suitable cleansing surfactants are generally anionic, amphoteric, betaine, or zwitterionic surfactants. Preferably, the anionic surfactants are alkyl ether or alkyl ether sulfates such as sodium lauryl sulfate, and other components described above.

Typical glossers are silicones. Suitable as silicones are volatile or nonvolatile nonionic silicone fluids, silicone resins, and silicone semisolids or solids. Volatile silicones are linear or cyclic silicones having a measureable vapor pressure, which is defined as a vapor pressure of at least 2 mm of mercury at 20° C. Also suitable are water insoluble nonvolatile silicone fluids including polyalkyl siloxanes, polyaryl siloxanes, polyalkylaryl siloxanes, polyether siloxane copolymers, amine-functional silicones, and mixtures thereof.

Typical oils to be used in hair compositions are organic oils, which often are esters. The organic oil component may also comprise glyceryl esters of fatty acids, or triglycerides, coconut oil, almond oil, apricot kernel oil, avocado oil, babassu oil, evening primrose oil, *camelina sativa* seed oil, grape seed oil, macadamia *ternifolia* seed oil, corn oil, meadowfoam seed oil, mink oil, olive oil, palm kernel oil, safflower oil, sesame oil, soybean oil, sunflower oil, wheat germ oil, and *camellia reticulata* seed oil. Also suitable as the oil component are sorbitan esters and glyceryl esters as described above. The cosmetic composition of the invention may contain from 0.05 to 5%, preferably 0.5 to 5% by weight of at least one oil component.

The composition of the invention can contain from 0.1 to 10% by weight, preferably from 0.2 to 5% by weight, more preferably from 0.5 to 5% by weight of at least one rheology modifying agent, in particular a gelling and thickening agent. Examples are cellulosic thickeners, for example, hydroxyethyl-cellulose, hydroxypropylcellulose, and carboxymethylcellulose, guar gum, such as hydroxypropylguar, gums of microbial origin, such as xanthan gum and scleroglucan gum, and synthetic thickeners, such as crosslinked homo- or copolymers of acrylic acid and/or of acrylamidopropanesulphonic acid. Other rheology modifying agents include fatty acid amides such as coconut diethanolamide and monoethanolamide, and oxyethylenated monoethanolamide of carboxylic acid alkyl ether.

Generally, the cosmetic composition according to the present invention is used for topical application to hair, but also skin or nail treatment is possible. In general, the cosmetic composition comprises 0.01 to 20% by weight of one or more oligoester ammonium salts as described above, in particular of formula (I), based on the total weight of the composition. More preferred, the oligoester ammonium salt is added in an amount from 0.05 to 20%, or from 0.1 to 15%, often 0.1 to 10% by weight based on the total weight of the composition.

In the case of hair conditioner compositions, the oligoester ammonium salt is added in an amount high enough to achieve at least one desired effect such as, for example, improved shine (gloss), detangling of hair or static charge reduction. Preferably, the hair conditioner composition comprises one or more oligoester ammonium salts of formula (I) in an amount of from 0.1 to 15% by weight based on the total weight of the composition. All percentages by weight given herein are based upon the total weight of the composition of the present invention, unless otherwise specified.

The hair conditioning composition of the present invention can also comprise as component (F) a fatty compound. The fatty compound is included in the composition at a level of from 0.1 to 20% by weight, preferably from 1.0 to 10% by weight. The fatty compound is selected from the group consisting of fatty alcohols (e.g. cetyl alkohol, stearyl alcohol or cetearyl alcohol), fatty acids, fatty alcohol derivatives, fatty acid derivatives, and mixtures thereof.

It is understood that the components disclosed can in some instances fall into more than one classification, e.g., some fatty alcohol derivatives can also be classified as fatty acid derivatives. However, a given classification, is not intended to be a limitation on that particular compound, but is done so for convenience of classification and nomenclature. Non-limiting examples are found in International Cosmetic Ingredient Dictionary and Handbook, Fourteenth Edition (2014), and CTFA Cosmetic Ingredient Handbook, Second Edition, 1992. Preferably, fatty alcohols have 14 to 30 or 16 to 22 carbon atoms. These fatty alcohols are saturated and can be linear or branched. Examples of fatty alcohols are cetyl alcohol, stearyl alcohol, behenyl alcohol, and mixtures thereof. Preferred fatty acids have from 10 to 30 or from 12 to 22 carbon atoms. These fatty acids can be saturated and can be linear or branched. Also included herein are salts of these fatty acids. Examples of fatty acids are lauric acid, palmitic acid, stearic acid, behenic acid, sebacic acid, and mixtures thereof.

The fatty alcohol derivatives and fatty acid derivatives useful herein include alkyl ethers of fatty alcohols, alkoxylated fatty alcohols, alkyl ethers of alkoxylated fatty alcohols, esters of fatty alcohols, fatty acid esters of compounds having esterifiable hydroxy groups, hydroxy-substituted fatty acids, and mixtures thereof. Examples of fatty alcohol derivatives and fatty acid derivatives include methyl stearyl ether; polyoxyethylene ethers of behenyl alcohol; ethyl stearate, cetyl stearate, cetyl palmitate, stearyl stearate, myristyl myristate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, poly glyceryl stearate, glyceryl monostearate, glyceryl distearate, glyceryl tristearate, and mixtures thereof.

The hair conditioning compositions of the present invention may comprise, in addition to the oligoester ammonium salt and at least one further component (F), an aqueous carrier. The level and species of the aqueous carrier are selected according to the compatibility with other components and other desired characteristic of the composition. The carrier includes water and water solutions of lower alkyl alcohols and polyhydric alcohols. The lower alkyl alcohols useful herein are monohydric alcohols having 1 to 6 carbons, often ethanol and/or isopropanol. The useful polyhydric alcohols include propylene glycol, hexylene glycol, glycerin, and propane diol. Preferably, the aqueous carrier is substantially water. Deionized water is preferably used. Water from natural sources, including minerals can also be used, depending on the desired characteristic of the cosmetic composition. Generally, the cosmetic compositions of the present invention can comprise up to 80%, often even up to 95% by weight of water.

Preferably, the compositions of the present invention contains as a further component a silicone compound. The composition can comprise up to 5% (e.g. 0.1 to 5%) by weight of a silicone compound. Suitable silicone compounds include polyalkyl or polyaryl siloxanes. The preferred silicone compounds are polydimethylsiloxane, polydiethylsiloxane, and polymethylphenylsiloxane, e.g. available from Wacker (Germany) or Dow Corning, such as Xiameter PMX DC 200. The silicone compounds may further be incorporated in the present composition in the form of an emulsion, wherein the emulsion is made by mechanical mixing with or without the aid of an additional surfactant selected from anionic surfactants, nonionic surfactants, cationic surfactants, and mixtures thereof.

The compositions of the present invention may also include as a further component (F), other components being suitable for rendering the composition more cosmetically or aesthetically acceptable or to provide them with additional usage benefits. Such other components can generally be used individually at levels of from 0.001% to 5% by weight. A wide variety of further components (F) can be formulated into the present composition. These include other conditioning agents, such as hydrolysed collagen, vitamin E, or panthenol, panthenyl ethyl ether, hydrolysed keratin, proteins, plant extracts, nutrients; and emollients such as PPG-3 myristyl ether, trimethyl pentanol hydroxyethyl ether; hair-fixative polymers such as amphoteric fixative polymers, cationic fixative polymers, anionic fixative polymers, nonionic fixative polymers, and silicone grafted copolymers; preservatives such as benzyl alcohol, methyl paraben, propyl paraben and imidazolidinyl urea; pH adjusting agents, such as citric acid, sodium citrate, succinic acid, phosphoric acid, sodium hydroxide, sodium carbonate; salts, in general, such as potassium acetate and sodium chloride; coloring agents; hair oxidizing (bleaching) agents, such as hydrogen peroxide, perborate and persulfate salts; hair reducing agents such as the thioglycolates; perfumes; and sequestering agents, such as disodium ethylene-diamine tetraacetate; ultraviolet and infrared screening and absorbing agents such as octyl salicylate; and anti-dandruff agents such as zinc pyrithione and salicylic acid.

The hair conditioning composition of the present invention may contain as a further component (F) a polysorbate for adjusting rheology, for example, polysorbate-20, polysorbate-21, polysorbate-40, polysorbate-60, and mixtures thereof. The polysorbate can be contained in the composition in amounts up to 5% (e.g. 0.1 to 5%) by weight.

The hair conditioning composition can also contain as a further component (F) a polypropylene glycol. Polypropylene glycols are those having a weight average molecular weight of from 200 to 100000 g/mol. The polypropylene glycol useful herein may be either water-soluble, water-insoluble, or may have a limited solubility in water, depending upon the degree of polymerization and whether other moieties are attached thereto. The desired solubility of the polypropylene glycol in water will depend in large part upon the form (e.g., leave-on, or rinse-off form) of the hair care composition.

For example, in a rinse-off hair care composition, it is preferred that the polypropylene glycol herein has a solubility in water at 25° C. of less than about 1 g/100 g water, more preferably a solubility in water of less than about 0.5 g/100 g water, and even more preferably a solubility in water of less than about 0.1 g/100 g water. The polypropylene glycol can be included in the hair conditioning composition of the present invention at a level of up to 10% by weight.

The hair conditioning composition can also contain, as a further component (F), low melting point oil selected from the group consisting of hydrocarbons having from 10 to 40 carbon atoms; unsaturated fatty alcohols having from 10 to 30 carbon atoms such as oleyl alcohol; unsaturated fatty acids having from about 10 to about 30 carbon atoms; fatty acid derivatives; fatty alcohol derivatives; ester oils such as pentaerythritol ester oils, trimethylol ester oils, citrate ester oils, and glyceryl ester oils; poly [alpha]-olefin oils; and mixtures thereof. Preferred low melting point oils herein are selected from the group consisting of: ester oils such as pentaerythritol ester oils, trimethylol ester oils, citrate ester oils, and glyceryl ester oils; poly [alpha]-olefin oils; and mixtures thereof, Particularly useful pentaerythritol ester oils and trimethylol ester oils herein include pentaerythritol tetraisostearate, pentaerythritol tetraoleate, trimethylolpropane triisostearate, trimethylolpropane trioleate, and mixtures thereof. Particularly useful glyceryl ester include triisostearin, triolein and trilinolein.

The hair conditioning composition can also contain, as a further component (F), a cationic polymer. Cationic polymers useful herein are those having an number average molecular weight of at least about 5000, typically from 10000 to 10 million (g/mol). Suitable cationic polymers include, for example, copolymers of vinyl monomers having cationic amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone, and vinyl pyrrolidone. Other suitable spacer monomers include vinyl esters, vinyl alcohol, maleic anhydride, propylene glycol, and ethylene glycol. Other suitable cationic polymers useful herein include, for example, cationic celluloses, cationic starches, and cationic guar gums. Commercially available cationic guar polymers are e.g. Jaguar® from Rhodia or Solvay.

The hair conditioning compositions of the present invention can be in the form of rinse-off products or leave-on products, can be opaque, and can be formulated in a wide variety of product forms, including creams, gels, emulsions, mousses and sprays. Preferably, the hair conditioner composition of the present invention is in the form of a rinse-off product.

The third aspect of the present invention is the use of the oligoester ammonium salt as described, in particular of formula (I) as defined above as an ingredient in cosmetic compositions, in particular hair conditioner compositions.

The fourth aspect is a method of preparing the cosmetic composition, in particular hair conditioner composition as defined above, comprising the step of mixing at least one oligoester ammonium salt, in particular of formula (I) as defined above, and at least one further component (F) as defined above.

The hair conditioning compositions can be prepared by any conventional method well known in the art. For example, they can be prepared as follows: deionized water is heated to 85° C. The oligoester ammonium salts (optionally purified) and one or more further components (F) are mixed into the water. The water is maintained at a temperature of about 85° C. until the components are homogenized, and no solids are observed. The mixture is then cooled to about 55° C. and maintained at this temperature. After it is homogenized, it is cooled to room temperature (20° C.).

The fifth aspect is a method of treating hair, comprising:
a) applying the hair conditioner composition as defined above onto wet hair, and then
b) removing the hair conditioner composition from the hair.

The hair conditioner composition as defined above can either be used on pre-cleaned hair or without pre-treatment. Preferably, the hair is being washed with shampoo prior to the application of the conditioner composition.

Thus, in at least one embodiment of fifth aspect of the present invention, the method of treating hair comprises:
(a) applying a shampoo composition onto the hair; and then
(b) washing the hair with the shampoo composition; and then
(c) removing the shampoo composition from the hair; and then
(d) applying the conditioner composition onto wet hair; and then removing the conditioner composition from the hair.

The method of treating hair according to the present invention may also include one or more additional steps using commonly known compositions like, for example, a color altering composition, a developer composition, a pre-treatment composition and/or a post-treatment composition. Such commonly known compositions include well-known conventional additives being typically applied in hair treatment compositions, such as coloring agents, basifying and acidifying agents, buffers, thickening agents, gelling agents, rheological modifiers, antioxidants, fragrances and chelating agents.

The preparation of the oligoester ammonium salt of general formula (I) can be achieved by methods known to those skilled in the art, for example, by
(i) firstly contacting the components of a reaction mixture (a) to (d) under increased temperature of 80 to 220°, in particular 150 to 210° C. by continuously removing of reaction water:
0.5 to 3.0 molar equivalents, often 0.75 to 3.0 molar equivalents of a diethanolamine compound represented by the formula (a)

(a)

wherein $R^3$ is a linear or branched $C_1$-$C_6$-alkyl group, preferably a linear or branched $C_1$-$C_4$-alkyl group, more preferably is methyl or ethyl;
0.5 to 1.5 molar equivalents of a dicarboxylic acid represented by the formula (b)

(b)

wherein $R^2$ is a linear or branched $C_1$-$C_{10}$-alkylene group or a linear or branched $C_2$-$C_{10}$-alkenylene group, preferably is a $C_2$-$C_8$-alkylene, more preferably is a $C_4$-alkylene group;
0.5 to 1.5 molar equivalents of an organic triol represented by the formula (c1) or (c2)

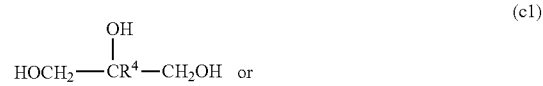

(c1)

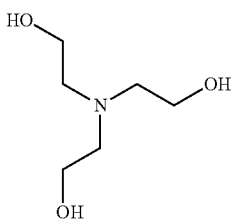

(c2)

wherein $R^4$ is hydrogen or a linear or branched $C_1$-$C_4$-alkyl or hydroxyl-$C_1$-$C_4$-alkyl group, preferably is hydrogen, methyl or ethyl, more preferably $R^4$ is hydrogen;

1.0 molar equivalent of a monocarboxylic acid represented by formula (d)

$$R^1\!-\!COOH \qquad (d)$$

wherein $R^1$ is a linear or branched $C_{12}$-$C_{24}$-alkyl or linear or branched $C_{12}$-$C_{24}$-alkenyl group, preferably a linear or branched $C_{12}$-$C_{22}$-alkyl or linear or branched $C_{12}$-$C_{22}$-alkenyl group, more preferably is $C_{20}$-$C_{22}$-alkyl;

(ii) reacting the oligoester product of step (i) with a quarternization agent (e), preferably from the group of commonly known alkylating agents such as dimethyl sulfate, diethyl sulfate and alkyl halides;

and then (iii) optionally removing and purifying the at least one oligoester ammonium salt.

Suitable alkylating agents are, for example, dimethyl sulfate, diethyl sulfate, dimethyl carbonate, diethyl carbonate, and alkyl halides, like methyl chloride, ethyl chloride, methyl bromide, ethyl bromide, methyl iodide or ethyl iodide.

The contacting step is carried out under conditions sufficient to produce oligoester amine, wherein n is an integer from 1 to about 30. The components of the reaction mixture can be contacted either sequentially or simultaneously. Preferably, the component (a), said dicarboxylic acid (b), said polyol (c) and said monocarboxylic acid (d) are contacted in the molar ratios described. Preferably, the contacting is carried out in the presence of an esterification catalyst, such as, a Brönstedt or Lewis acid catalyst, or a metal catalyst. Examples are hypophosphorous acid, p-toluene sulfonic acid, titanium tetrabutylate or Fascat®.

The invention also relates to a multiple-part kit of hair cleaning and hair conditioning compositions. The term "kit" includes items that are either sold or packaged together. The multiple-part kit may be distributed to end users through salons, but one aspect of the invention involves distributing the kits to consumers through retail sales channels such as drugstores, cosmetic stores and on-line stores. The kit comprises separate compartments with formulations for a shampoo and a conditioning treatment. The term "compartment" refers to any receptacle, regardless of shape, material or closure, which serves a containing function. The term includes the interior of a tube, sack, can, tub, bottle, packet, envelope or other vessel. The components of the multiple-part kit may be contained in a single receptacle, or may be divided amongst multiple receptacles. The multiple-part kit can additionally comprise a compartment with a composition to color the hair and/or a composition to moisturize and maintain the quality of the treated hair.

For bleached or colored hair, additional compartments in the multiple-part kit are advantageous. There is a high need for a hair cleaning and hair conditioning kit, that is easy to use and that provides a consumer specialized care regimen to preserve the condition of the hair. The invention provides all this in one multiple-part kit with all the components needed to maintain the condition of the hair for several weeks. The kit may include at least one compartment containing a pre-treatment composition.

The invention is further illustrated by the following non-limiting examples.

EXAMPLE 1: PREPARATION OF OLIGOESTER PRECURSOR

Methyl diethanol amine (component (a), 119.2 g, 1.0 mol), behenic acid (component (d), 510.9 g, 1.5 mol), adipic acid (component (b), 219.2 g, 1.5 mol) and glycerol (component (c), 138.16 g, 1.5 mol) were charged in a 2 L flask equipped with a stirrer, distillation apparatus and thermometer under an atmosphere of nitrogen. The reaction mixture was heated to 160° C. and the distillation of reaction water started. The temperature was increased to 206° C. when the head temperature decreased. The reaction water was continually removed from the reaction mixture by distillation at 160-206° C. over a period of 5 h.

The product (782 g) was obtained as clear, brown liquid (acid value: 10.2 mg KOH/g; Bas-N: 1.50%; $M_n$=1246 g/mol, $M_w$=1354 g/mol).

EXAMPLE 2: OLIGOESTER AMMONIUM SALT

The oligoester of Example 1 (150.0 g) was charged in a 1 L flask equipped with a stirrer, distillation apparatus and thermometer under an atmosphere of nitrogen and heated to 85° C. Dimethyl sulfate (10.1 g, 0.08 mol, 0.5 equivalents/nitrogen atom in the oligoester) was added dropwise over a period of 15 minutes. The reaction mixture was stirred for 5 h at 90° C. The product (151 g) was obtained as light brown solid (Bas.-N: 0.70%).

EXAMPLE 3: OLIGOESTER AMMONIUM SALT

The oligoester of Example 1 (150.0 g) was charged in a 1 L flask equipped with a stirrer, distillation apparatus and thermometer under an atmosphere of nitrogen and heated to 85° C. Dimethyl sulfate (19.9 g, 0.15 mol, 0.98 equivalents/nitrogen atom in the oligoester) was added dropwise over a period of 15 minutes. The reaction mixture was stirred for 5 h at 90° C. The product (154 g) was obtained as light brown solid (Bas.-N: 0.11%).

EXAMPLE 4: PREPARATION OF OLIGOESTER PRECURSOR

Methyl diethanol amine (119.2 g, 1.0 mol), behenic acid (510.9 g, 1.5 mol), adipic acid (219.2 g, 1.5 mol) and triethanolamine (223.8 g, 1.5 mol) were charged in a 2 L flask equipped with a stirrer, distillation apparatus and thermometer under an atmosphere of nitrogen. The reaction mixture was heated to 160° C. for 3 h and reaction water was removed from the reaction mixture by distillation. Afterwards the reaction mixture was heated to 200-205° C. for 8 h and reaction water was removed from the reaction mixture by distillation. The product (963 g) was obtained as brown wax (acid value: 1.7 mg KOH/g; Bas-N: 3.49%; $M_n$=1756 g/mol, $M_w$=2139 g/mol).

EXAMPLE 5 OLIGOESTER AMMONIUM SALT (OAS)

The oligoester of Example 4 (300.0 g) was charged in a 1 L flask equipped with a stirrer, distillation apparatus and thermometer under an atmosphere of nitrogen and heated to 85° C. Dimethyl sulfate (92.2 g, 0.73 mol, 0.98 equivalents/nitrogen atom in the Oligoester) was added dropwise over a period of 20 minutes. During the addition, the resulting product mixture became highly viscous and butyl diglycol (98.1 g) was added. The reaction mixture was stirred for 5 h at 85° C. The product (400 g, 80% active content) was obtained as brown wax (Bas.-N: 0.01%).

EXAMPLE 6: OLIGOESTER AMMONIUM SALT

The oligoester of Example 4 (330.0 g) was charged in a 1 L flask equipped with a stirrer, distillation apparatus and thermometer under an atmosphere of nitrogen and heated to 85° C. Dimethyl sulfate (51.8 g, 0.41 mol, 0.5 equivalents/nitrogen atom in the oligoester) was added dropwise over a period of 20 minutes. During the addition, the resulting product mixture became highly viscous and butyl diglycol (42.4 g) was added. The reaction mixture was stirred for 5 h at 85° C. The product (380 g, 90% active content) was obtained as brown wax (Bas.-N: 1.31%).

EXAMPLE 7: PREPARATION OF OLIGOESTER PRECURSOR

Methyl diethanol amine (238.4 g, 2.0 mol), behenic acid (340.4 g, 1.0 mol), adipic acid (219.2 g, 1.5 mol) and glycerol (138.5 g, 1.5 mol) were charged in a 2 L flask equipped with a stirrer, distillation apparatus and thermometer under an atmosphere of nitrogen. The reaction mixture was heated to 160° C. for 2 h and reaction water was removed from the reaction mixture by distillation. Afterwards the reaction mixture was heated to 200-205° C. for 7 h and reaction water was removed from the reaction mixture by distillation. The product (810 g) was obtained as brown wax (acid value: 3 mg KOH/g; Bas-N: 2.85%; $M_n$=1314 g/mol; $M_w$=1445 g/mol).

EXAMPLE 8: OLIGOESTER AMMONIUM SALT

The oligoester of Example 7 (260.0 g) was charged in a 1 L flask equipped with a stirrer, distillation apparatus and thermometer under an atmosphere of nitrogen and heated to 85° C. Dimethyl sulfate (65.3 g, 0.52 mol, 0.98 equivalents/nitrogen atom in the oligoester) was added dropwise over a period of 20 minutes. During the addition, the resulting product mixture became highly viscous and butyl diglycol (81.3 g) was added. The reaction mixture was stirred for 5 h at 85° C. The product (370 g, 80% active content) was obtained as brown wax (Bas.-N<0.01%).

EXAMPLE 9: OLIGOESTER AMMONIUM SALT

The oligoester of Example 7 (280.0 g) was charged in a 1 L flask equipped with a stirrer, distillation apparatus and thermometer under an atmosphere of nitrogen and heated to 85° C. Dimethyl sulfate (35.9 g, 0.29 mol, 0.5 equivalents/nitrogen atom in the oligoester) was added dropwise over a period of 20 minutes. During the addition, the resulting product mixture became highly viscous and butyl diglycol (35.1 g) was added. The reaction mixture was stirred for 5 h at 85° C. The product (320 g, 90% active content) was obtained as brown wax (Bas.-N=1.04%).

EXAMPLE 10: PREPARATION OF OLIGOESTER PRECURSOR

Methyl diethanol amine (238.4 g, 2.0 mol), behenic acid (681.2 g, 2.0 mol), adipic acid (219.2 g, 1.5 mol) and glycerol (138.2 g, 1.5 mol) were charged in a 2 L flask equipped with a stirrer, distillation apparatus and thermometer under an atmosphere of nitrogen. The reaction mixture was heated to 170° C. for 2 h and reaction water was removed from the reaction mixture by distillation. Afterwards the reaction mixture was heated to 190° C. for 1 h, then to 200° C. for 1 h and then to 210° C. for 1 h. During heating, reaction water was continually removed from the reaction mixture by distillation. The product (1127 g) was obtained as brown wax (Acid value: 2.9 mg KOH/g; Bas-N: 2.24%; $M_n$=1029 g/mol; $M_w$=1329 g/mol).

EXAMPLE 11: OLIGOESTER AMMONIUM SALT

The oligoester of Example 10 (255.1 g) was charged in a 1 L flask equipped with a stirrer, distillation apparatus and thermometer under an atmosphere of nitrogen and heated to 60° C. Dimethyl sulfate (50.4 g, 0.40 mol, 0.98 equivalents/nitrogen atom in the oligoester) was added dropwise over a period of 25 minutes. During the addition, the resulting product mixture became highly viscous and butyl diglycol (30.1 g) was added. The reaction mixture was heated to 80° C. and stirred at this temperature for 0.5 h. Subsequently the reaction mixture was heated to 90° C. and stirred at this temperature for 4.5 h. The product (288 g, 90% active content) was obtained as brown solid (Bas.-N<0.01%).

EXAMPLE 12: PREPARATION OF OLIGOESTER PRECURSOR

Methyl diethanol amine (119.2 g, 1.0 mol), behenic acid (340.6 g, 1.0 mol), adipic acid (219.2 g, 1.5 mol) and glycerol (138.2 g, 1.5 mol) were charged in a 2 L flask equipped with a stirrer, distillation apparatus and thermometer under an atmosphere of nitrogen. The reaction mixture was heated to 170° C. for 1 h and reaction water was removed from the reaction mixture by distillation. Afterwards the reaction mixture was heated to 190° C. for 1 h, then to 200° C. for 1 h and then to 210° C. for 0.5 h. During heating, reaction water was continually removed from the reaction mixture by distillation. The product (703 g) was obtained as brown wax (Acid value: 5.2 mg KOH/g; Bas-N: 1.66%; $M_n$=1176 g/mol; $M_w$=1610 g/mol).

EXAMPLE 13: OLIGOESTER AMMONIUM SALT

The oligoester of Example 12 (253.0 g) was charged in a 1 L flask equipped with a stirrer, distillation apparatus and thermometer under an atmosphere of nitrogen and heated to 60° C. Dimethyl sulfate (37.3 g, 0.29 mol, 0.98 equivalents/nitrogen atom in the oligoester) was added dropwise over a period of 15 minutes. During the addition, the resulting product mixture became highly viscous and butyl diglycol (41.2 g) was added. The reaction mixture was heated to 80° C. and stirred at this temperature for 1 h. Afterwards the temperature was increased to 90° C. and the reaction mixture was stirred at this temperature for additional 4 h. The product (303 g, 88% active content) was obtained as brown solid (Bas.-N=0.02%).

EXAMPLE 14: PREPARATION OF OLIGOESTER PRECURSOR

Methyl diethanol amine (119.2 g, 1.0 mol), behenic acid (170.3 g, 0.5 mol), adipic acid (109.6 g, 0.75 mol) and glycerol (23.0 g, 0.25 mol) were charged in a 2 L flask equipped with a stirrer, distillation apparatus and thermometer under an atmosphere of nitrogen. The reaction mixture was heated to 170° C. for 1 h and reaction water was removed from the reaction mixture by distillation. Afterwards the reaction mixture was heated to 180° C. for 2 h, then to 190° C. for 2 h, then to 200° C. for 2 h and then to 210° C. for 1 h. During heating, reaction water was continually removed from the reaction mixture by distillation. The product (343 g) was obtained as brown soil (Acid value: 2.6 mg KOH/g; Bas-N: 3.21%; $M_n$=1892 g/mol; $M_w$=3038 g/mol).

EXAMPLE 15: OLIGOESTER AMMONIUM SALT

The oligoester of Example 14 (150.0 g) was charged in a 1 L flask equipped with a stirrer, distillation apparatus and thermometer under an atmosphere of nitrogen and heated to 60° C. Dimethyl sulfate (42.5 g, 0.34 mol, 0.98 equivalents/nitrogen atom in the oligoester) was added dropwise over a period of 30 minutes in a way that the temperature did not exceed 80° C. Due to the high viscosity of the resulting product mixture, butyl diglycol (57.5 g) was added in portions during the addition of dimethyl sulfate. The temperature was increased to 80° C. and the reaction mixture was stirred at this temperature for 1 h. Afterwards the temperature was increased to 90° C. and the reaction mixture was stirred at this temperature for additional 4 h. The product (349 g, 77% active content) was obtained as brown solid (Bas.-N<0.01%).

EXAMPLE 16: PREPARATION OF OLIGOESTER PRECURSOR

Methyl diethanol amine (178.8 g, 1.5 mol), behenic acid (170.3 g, 0.5 mol), adipic acid (109.6 g, 0.75 mol) and glycerol (69.1 g, 0.75 mol) were charged in a 2 L flask equipped with a stirrer, distillation apparatus and thermometer under an atmosphere of nitrogen. The reaction mixture was heated to 170° C. for 2 h and reaction water was removed from the reaction mixture by distillation. Afterwards the reaction mixture was heated to 190° C. for 1.5 h and then to 200° C. for 1 h. During heating, reaction water was continually removed from the reaction mixture by distillation. The product (391 g) was obtained as brown solid (Acid value: 1.2 mg KOH/g; Bas-N: 2.98%; $M_n$=908 g/mol; $M_w$=1360 g/mol).

EXAMPLE 17: OLIGOESTER AMMONIUM SALT

The oligoester of Example 16 (234.7 g) was charged in a 1 L flask equipped with a stirrer, distillation apparatus and thermometer under an atmosphere of nitrogen and heated to 60° C. Dimethyl sulfate (61.8 g, 0.49 mol, 0.98 equivalents/nitrogen atom in the oligoester) was added dropwise over a period of 45 minutes. The addition was stopped for three times and cooled to 70° C. to prevent reaction temperatures higher than 80° C. in the reaction mixture. During the addition, the resulting product mixture became highly viscous and butyl diglycol (69.6 g) was added in portions. The reaction mixture was heated to 90° C. and stirred at this temperature for 5 h. The product (349 g, 81% active content) was obtained as brown solid (Bas.-N=0.06%).

EXAMPLE 18: PREPARATION OF OLIGOESTER PRECURSOR

Methyl diethanol amine (178.8 g, 1.5 mol), behenic acid (170.3 g, 0.5 mol), adipic acid (109.6 g, 0.75 mol) and glycerol (46.1 g, 0.5 mol) were charged in a 2 L flask equipped with a stirrer, distillation apparatus and thermometer under an atmosphere of nitrogen. The reaction mixture was heated to 170° C. for 2 h and reaction water was removed from the reaction mixture by distillation. Afterwards the reaction mixture was heated to 190° C. for 1 h and then to 200° C. for 1 h. During heating, reaction water was continually removed from the reaction mixture by distillation. The product (446 g) was obtained as brown solid (Acid value: 2.9 mg KOH/g; Bas-N: 4.12%; $M_w$=985 g/mol).

EXAMPLE 19: OLIGOESTER AMMONIUM SALT

The oligoester of Example 18 (237.9 g) was charged in a 1 L flask equipped with a stirrer, distillation apparatus and thermometer under an atmosphere of nitrogen and heated to 60° C. Dimethyl sulfate (86.5 g, 0.69 mol, 0.98 equivalents/nitrogen atom in the oligoester) was added dropwise over a period of 45 minutes. The addition was stopped for three times and cooled to 70° C. to prevent reaction temperatures higher than 80° C. in the reaction mixture. During the addition, the resulting product mixture became highly viscous and butyl diglycol (62.3 g) was added. The reaction mixture was heated to 90° C. and stirred at this temperature for 5 h. The product (372 g, 84% active content) was obtained as brown solid (Bas.-N=0.03%).

EXAMPLE 20: PREPARATION OF OLIGOESTER PRECURSOR

Methyl diethanol amine (178.8 g, 1.5 mol), behenic acid (170.3 g, 0.5 mol), adipic acid (73.1 g, 0.5 mol) and glycerol (69.1 g, 0.75 mol) were charged in a 2 L flask equipped with a stirrer, distillation apparatus and thermometer under an atmosphere of nitrogen. The reaction mixture was heated to 170° C. for 1 h and reaction water was removed from the reaction mixture by distillation. Afterwards the reaction mixture was heated to 190° C. for 2 h, then to 200° C. for 1 h and then to 210° C. for 1 h. During heating, reaction water was continually removed from the reaction mixture by distillation. The product (386 g) was obtained as brown solid (Acid value: 1.1 mg KOH/g; Bas-N: 3.39%; $M_n$=768 g/mol; $M_w$=1037 g/mol).

EXAMPLE 21: OLIGOESTER AMMONIUM SALT

The oligoester of Example 20 (150.0 g) was charged in a 1 L flask equipped with a stirrer, distillation apparatus and thermometer under an atmosphere of nitrogen and heated to 60° C. Dimethyl sulfate (44.8 g, 0.36 mol, 0.98 equivalents/nitrogen atom in the oligoester) was added dropwise over a period of 30 minutes. During the addition, the resulting product mixture became highly viscous and butyl diglycol (41.1 g) was added. The reaction mixture was heated to 80° C. and stirred at this temperature for 1 h. Afterwards the temperature was increased to 90° C. and the reaction mixture was stirred at this temperature for additional 4 h. The product (210 g, 83% active content) was obtained as brown solid (Bas.-N not detected).

EXAMPLE 22: PREPARATION OF OLIGOESTER PRECURSOR

Methyl diethanol amine (178.8 g, 1.5 mol), behenic acid (170.3 g, 0.5 mol), adipic acid (36.5 g, 0.25 mol) and glycerol (69.1 g, 0.75 mol) were charged in a 2 L flask equipped with a stirrer, distillation apparatus and thermometer under an atmosphere of nitrogen. The reaction mixture was heated to 170° C. for 1 h and reaction water was removed from the reaction mixture by distillation. Afterwards the reaction mixture was heated to 190° C. for 2 h and then to 200° C. for 1.5 h. During heating, reaction water was continually removed from the reaction mixture by distillation. The product (382 g) was obtained as brown wax (Acid value: 2.6 mg KOH/g; Bas-N: 3.39%; $M_w$=842 g/mol).

EXAMPLE 23: OLIGOESTER AMMONIUM SALT (OAS)

The oligoester of Example 22 (150.0 g) was charged in a 1 L flask equipped with a stirrer, distillation apparatus and thermometer under an atmosphere of nitrogen and heated to 60° C. Dimethyl sulfate (44.8 g, 0.36 mol, 0.98 equivalents/nitrogen atom in the oligoester) was added dropwise over a period of 30 minutes. During the addition, the resulting product mixture became highly viscous and butyl diglycol (17.5 g) was added. The reaction mixture was heated to 80° C. and stirred at this temperature for 1 h. Afterwards the temperature was increased to 90° C. and the reaction mixture was stirred at this temperature for additional 4 h. The product (177 g, 92% active content) was obtained as brown solid (Bas.-N<0.17%).

EXAMPLE 24: PREPARATION OF OLIGOESTER PRECURSOR

Methyl diethanol amine (178.8 g, 1.5 mol), behenic acid (170.3 g, 0.5 mol), sebacic acid (220.8 g, 0.75 mol) and glycerol (69.1 g, 0.75 mol) were charged in a 2 L flask equipped with a stirrer, distillation apparatus and thermometer under an atmosphere of nitrogen. The reaction mixture was heated to 170° C. for 1 h and reaction water was removed from the reaction mixture by distillation. Afterwards the reaction mixture was heated to 190° C. for 2 h and then to 200° C. for 2 h. During heating, reaction water was continually removed from the reaction mixture by distillation. The product (510 g) was obtained as brown solid (Acid value: 2.6 mg KOH/g; Bas-N: 2.91%; $M_n$=1405 g/mol; $M_w$=2205 g/mol).

EXAMPLE 25: OLIGOESTER AMMONIUM SALT

The oligoester of Example 24 (150.0 g) was charged in a 1 L flask equipped with a stirrer, distillation apparatus and thermometer under an atmosphere of nitrogen and heated to 60° C. Dimethyl sulfate (38.6 g, 0.31 mol, 0.98 equivalents/nitrogen atom in the oligoester) was added dropwise over a period of 30 minutes. During the addition, the resulting product mixture became highly viscous and butyl diglycol (15.9 g) was added. The reaction mixture was heated to 80° C. and stirred at this temperature for 1 h. Afterwards the temperature was increased to 90° C. and the reaction mixture was stirred at this temperature for additional 4 h. The product (182 g, 92% active content) was obtained as brown solid (Bas.-N<0.07%).

EXAMPLES 26 TO 66: PREPARATION OF HAIR CONDITIONER COMPOSITIONS

The hair conditioner compositions of examples 26 to 66 are prepared by mixing the components, as listed in Table 1. All cosmetic compositions are creamy white liquids with appearance and physical properties similar to commercially available rinse-off hair conditioner products. The pH-values of the formulations are adjusted to 3.5 to 4.5. INCI names are provided for each ingredient. Xiameter PMX-200 is e.g. a silicone fluid (Dimethicone). CE=comparative example.

TABLE 1

Hair conditioner compositions, components are given in weight %.

| Ingredient | 26 (CE) | 27 | 28 | 29 | 30 | 31 (CE) | 32 (CE) |
|---|---|---|---|---|---|---|---|
| Cetearyl Alcohol | 4.0 | 4.0 | 4.0 | 4.0 | 4.0 | 4.0 | 4.0 |
| CTAC | 0.5 | 0.5 | 0.2 | 0.5 | 0.2 | 0.3 | 0.2 |
| Example 1 | 2.0 | — | — | — | — | — | — |
| Example 2 | — | 2.0 | 1.8 | — | — | — | — |
| Example 3 | — | — | — | 2.0 | 1.8 | — | — |
| Example 4 | — | — | — | — | — | 1.7 | 1.8 |
| Example 5 | — | — | — | — | — | — | — |
| Example 6 | — | — | — | — | — | — | — |
| Example 7 | — | — | — | — | — | — | — |
| Example 8 | — | — | — | — | — | — | — |
| Example 9 | — | — | — | — | — | — | — |
| Xiameter PMX-200 | 0.2 | 0.2 | 0.2 | 0.2 | 0.2 | 0.2 | 0.2 |
| Preservative | q.s. | q.s. | q.s. | q.s. | q.s. | q.s. | q.s. |
| Water | Ad. 100 | Ad. 100 | Ad. 100 | Ad. 100 | Ad. 100 | Ad. 100 | Ad. 100 |

| Ingredient | 33 | 34 | 35 (CE) | 36 (CE) | 37 | 38 | 39 (CE) |
|---|---|---|---|---|---|---|---|
| Cetearyl Alcohol | 4.0 | 4.0 | 4.0 | 4.0 | 4.0 | 4.0 | 4.0 |

TABLE 1-continued

Hair conditioner compositions, components are given in weight %.

| Ingredient | | | | | | | |
|---|---|---|---|---|---|---|---|
| CTAC | 0.2 | 0.2 | 0.3 | 0.2 | 0.2 | 0.2 | 0.2 |
| Example 1 | — | — | — | — | — | — | 1.8 |
| Example 2 | — | — | — | — | — | — | — |
| Example 3 | — | — | — | — | — | — | — |
| Example 4 | — | — | — | — | — | — | — |
| Example 5 | 1.8 | — | — | — | — | — | — |
| Example 6 | — | 1.8 | — | — | — | — | — |
| Example 7 | — | — | 1.7 | 1.8 | — | — | — |
| Example 8 | — | — | — | — | 1.8 | — | — |
| Example 9 | — | — | — | — | — | 1.8 | — |
| Xiameter PMX-200 | 0.2 | 0.2 | 0.2 | 0.2 | 0.2 | 0.2 | 0.2 |
| Preservative | q.s. | q.s. | q.s. | q.s. | q.s. | q.s. | q.s. |
| Water | Ad. 100 | Ad. 100 | Ad. 100 | Ad. 100 | Ad. 100 | Ad. 100 | Ad. 100 |

| Ingredient | Example 40 | 41 | 42 | 43 | 44 | 45 | 46 |
|---|---|---|---|---|---|---|---|
| Cetearyl Alcohol | 4.0 | 4.0 | 4.0 | 4.0 | 4.0 | 4.0 | 4.0 |
| CTAC | — | 0.2 | — | 0.2 | — | 0.2 | — |
| Example 13 | 2.0 | — | — | — | — | — | — |
| Example 15 | — | 1.8 | 2.0 | — | — | — | — |
| Example 17 | — | — | — | 1.8 | 2.0 | — | — |
| Example 19 | — | — | — | — | — | 1.8 | 2.0 |
| Example 21 | — | — | — | — | — | — | — |
| Example 25 | — | — | — | — | — | — | — |
| Xiameter PMX-200 | 0.2 | 0.2 | 0.2 | 0.2 | 0.2 | 0.2 | 0.2 |
| Preservative | q.s. | q.s. | q.s. | q.s. | q.s. | q.s. | q.s. |
| Water | Ad. 100 | Ad. 100 | Ad. 100 | Ad. 100 | Ad. 100 | Ad. 100 | Ad. 100 |

| Ingredient | Example 47 | 48 | 49 | 50 | 51 |
|---|---|---|---|---|---|
| Cetearyl alcohol | 4.0 | 4.0 | 4.0 | 4.0 | 4.0 |
| CTAC | 0.2 | 0.2 | — | — | — |
| Example 5 | — | — | — | 2.0 | — |
| Example 8 | — | — | — | — | 2.0 |
| Example 13 | — | — | — | — | — |
| Example 15 | — | — | — | — | — |
| Example 17 | — | — | — | — | — |
| Example 19 | — | — | — | — | — |
| Example 21 | 1.8 | — | — | — | — |
| Example 25 | — | 1.8 | 2.0 | — | — |
| Xiameter PMX-200 | 0.2 | 0.2 | 0.2 | — | — |
| Preservative | q.s. | q.s. | q.s. | q.s | q.s |
| Water | Ad. 100 | Ad. 100 | Ad. 100 | Ad. 100 | Ad. 100 |

| Ingredient | Example 52 | 53 | 54 | 55 | 56 | 57 | 58 |
|---|---|---|---|---|---|---|---|
| Cetearyl Alcohol | 4.0 | 4.0 | 4.0 | — | — | — | 3.50 |
| Cetyl Alcohol | — | — | — | 4.0 | 4.0 | 4.0 | — |
| Stearyl Alcohol | — | — | — | 1.0 | 1.0 | 1.0 | — |
| Example 3 | 0.5 | — | — | 1.0 | — | — | 1.5 |
| Example 5 | — | 0.5 | — | — | 1.0 | — | — |
| Example 6 | — | — | 0.5 | — | — | 1.0 | — |
| Xiameter PMX-200 | 2.0 | 2.0 | 2.0 | — | — | — | — |
| Dow 2-8566 Amino Fluid (Amodimethicone) | — | — | — | 2.5 | 2.5 | 2.5 | — |
| Wacker Fluid NH 130D (Polydimethylsiloxane, 3-aminopropyl terminated) | — | — | — | — | — | — | — |
| Stearamidopropyl dimethylamine | 1.5 | 1.5 | 1.5 | — | — | — | — |

TABLE 1-continued

Hair conditioner compositions, components are given in weight %.

| Ingredient | | | | | | | |
|---|---|---|---|---|---|---|---|
| Hydroxyethyl-cellulose | — | — | — | 1.0 | 1.0 | 1.0 | — |
| Trideceth 6 | — | — | — | 0.5 | 0.5 | 0.5 | — |
| Crodamol SS (cetyl esters wax) | — | — | — | — | — | — | 0.8 |
| Trehalose | 0.8 | 0.8 | 0.8 | — | — | — | — |
| Niacinamide | — | — | — | — | — | — | 0.5 |
| Preservative | q.s. | q.s. | q.s. | q.s. | q.s. | q.s. | q.s. |
| Water | Ad. 100 | Ad. 100 | Ad. 100 | Ad. 100 | Ad. 100 | Ad. 100 | Ad. 100 |

| | Example | | | | | | |
|---|---|---|---|---|---|---|---|
| Ingredient | 59 | 60 | 61 | 62 | 63 | 64 | 65 |
| Cetearyl Alcohol | 3.50 | 3.50 | — | — | — | 4.0 | 4.0 |
| Cetyl Alcohol | — | — | 0.8 | 0.8 | 0.8 | — | — |
| Stearyl Alcohol | — | — | 3.5 | 3.5 | 3.5 | — | — |
| Example 3 | — | — | 2.0 | — | — | 1.0 | — |
| Example 5 | 1.5 | — | — | 2.0 | — | — | 1.0 |
| Example 6 | — | 1.5 | — | — | 2.0 | — | — |
| Xiameter PMX-200 | — | — | — | — | — | 1.75 | 1.75 |
| Dow 2-8566 Amino Fluid (Amodimethicone) | — | — | — | — | — | — | — |
| Wacker Fluid NH 130D (Polydimethylsiloxane, 3-aminopropyl terminated) | — | — | 0.5 | 0.5 | 0.5 | — | — |
| Stearamidopropyl dimethylamine | — | — | — | — | — | 1.0 | 1.0 |
| Hydroxyethyl-cellulose | — | — | — | — | — | — | — |
| Trideceth 6 | — | — | — | — | — | — | — |
| Crodamol SS (cetyl esters wax) | 0.8 | 0.8 | — | — | — | — | — |
| Trehalose | — | — | — | — | — | — | — |
| Niacinamide | 0.5 | 0.5 | — | — | — | — | — |
| Preservative | q.s. | q.s. | q.s. | q.s. | q.s. | q.s. | q.s. |
| Water | Ad. 100 | Ad. 100 | Ad. 100 | Ad. 100 | Ad. 100 | Ad. 100 | Ad. 100 |

| Ingredient | Example 66 |
|---|---|
| Cetearyl Alcohol | 4.0 |
| Cetyl Alcohol | — |
| Stearyl Alcohol | — |
| Example 3 | — |
| Example 5 | — |
| Example 6 | 1.0 |
| Xiameter PMX-200 | 1.75 |
| Dow 2-8566 Amino Fluid (Amodimethicone) | — |
| Wacker Fluid NH 130D (Polydimethylsiloxane, 3-aminopropyl terminated) | — |
| Stearamidopropyl dimethylamine | 1.0 |
| Hydroxyethylcellulose | — |
| Trideceth 6 | — |
| Crodamol SS (cetyl esters wax) | — |
| Trehalose | — |
| Niacinamide | — |
| Preservative | q.s. |
| Water | Ad. 100 |

EXAMPLE 67: TESTING OF THE CONDITIONER COMPOSITIONS

The studies are conducted with hair swatches (using dark brown, straight European hair tresses from Kerling, 15 cm long, ca. 2.6 g hair each). Virgin hair (not chemically treated) and damaged (4 times bleached) hair are used.

Hair swatches are pre-treated (base wash with a 14% by weight sodium lauryl ether sulfate (SLES) solution), and then treated with one of the conditioner as described in examples 26 to 64. The following steps are used:
a) applying a shampoo formulation onto the hair;
b) washing the hair with the shampoo formulation;
c) removing the shampoo composition from the hair;
d) applying the conditioner composition of examples 26 to 64, onto the hair;
e) removing said conditioner composition from the hair.

The combing forces in wet and dry state are measured using a typically used instrument (Diastron (UK) MTT175), wet combing after rinsing off the conditioner, and dry combing after at least 12 hours of drying time in air at 22° C. The hair swatches are pre-combed three times before the measurement.

As benchmarks, analogous conditioner compositions are used containing cetrimmonium chloride (CTAC) or behentrimonium chloride (BTAC) at 2% by weight, active level, as listed in Table 2. The Table 3 then presents the wet (average) combing force (gmf force) for hair treated with selected conditioner compositions of examples 26 to 64 (see formulations in Table 1).

TABLE 2

Formulations of comparative Example (CE) hair conditioner compositions (active levels of ingredients in weight %, Silicone from Dow Corning (DC200)).

| Ingredient | Example (CE1) | Example (CE2) |
| --- | --- | --- |
| Cetearyl Alcohol | 4.0 | 4.0 |
| CTAC | 2.0 | — |
| BTAC (Behentrimonium Chloride) Example 1 | — | 2.0 |
| Xiameter PMX-200 | 0.2 | 0.2 |
| Preservative | q.s. | q.s. |
| Water | Ad. 100 | Ad. 100 |

TABLE 3

Wet combing force results of hair treated with conditioner compositions (Examples 30 to 64) compared to benchmark formulations (CE1 or CE2).

| Example | wet combing force, virgin hair (average), gmf | wet combing force, damaged hair (average), gmf |
| --- | --- | --- |
| CE1 | — | 12.1 |
| CE2 | 10.7 | — |
| Example 30 | 9.9 | — |
| Example 33 | 9.5 | — |
| Example 34 | 9.7 | — |
| Example 35 | 10.6 | — |
| Example 37 | 9.0 | — |
| Example 41 | 10.2 | — |
| Example 46 | 10.0 | 11.4 |
| Example 50 | 8.8 | 11.8 |
| Example 51 | 7.5 | — |
| Example 52 | 9.9 | 11.8 |
| Example 53 | 10.2 | 9.2 |
| Example 54 | 9.6 | 9.6 |
| Example 56 | — | 10.2 |
| Example 62 | 8.6 | — |
| Example 66 | 9.3 | — |

Table 4 presents the dry (maximum) combing force (gmf force) for hair treated with selected conditioner compositions of Example 33 to Example 46. As benchmark, comparative example CE1 is used (formulation in Table 2).

TABLE 4

Dry combing force results of hair treated with conditioner compositions (Examples 33 to Example 46), compared to benchmark formulation CE1.

| Example | dry combing force, virgin hair (max), gmf | dry combing force, damaged hair (max), gmf |
| --- | --- | --- |
| CE1 | 140.8 | 117.2 |
| Example 33 | — | 116.4 |
| Example 36 | 132.0 | — |
| Example 37 | 135.1 | 77.9 |
| Example 38 | 111.7 | — |
| Example 46 | — | 106.5 |
| Example 50 | 67.3 | 55.3 |
| Example 51 | 79.5 | 45.8 |

The dry hair after treatments with all conditioner compositions of examples 26 to 64 showed good tactile results and led to nice hair appearance. In particular, conditioner compositions of examples 29 to 33 and 35 to 37 produced an effect of very soft hair.

After using the method of treating hair with the conditioning composition, comprising an optional pre-treatment with silicone-free shampoo and a conditioner treatment, the hair probes are tested for hair shine (using a classical testing with Samba Hair System, from Bossa Nova Tech). This measurement technique allows for quantitative evaluation of the light intensity reflected from hair swatches mounted on a drum in a half-circle arrangement.

Results of the shine measurements are illustrated in Table 5, for hair swatches treated with compositions of examples 26 to 49, which in general show stronger shine than the prior art formulation CE1.

TABLE 5

Hair shine results for swatches treated with conditioner compositions

| Example | hair shine, virgin hair | hair shine, damaged hair |
| --- | --- | --- |
| CE 1 | 15.5 | 6.8 |
| Example 26 | 16.7 | — |
| Example 27 | 16.0 | — |
| Example 28 | 19.0 | 7.4 |
| Example 29 | 16.1 | — |
| Example 30 | 19.3 | — |
| Example 31 | 16.7 | — |
| Example 32 | 17.5 | — |
| Example 33 | 18.4 | 7.4 |
| Example 34 | 17.5 | — |
| Example 35 | 18.4 | — |
| Example 36 | 18.2 | — |

TABLE 5-continued

Hair shine results for swatches treated with conditioner compositions

| Example | hair shine, virgin hair | hair shine, damaged hair |
|---|---|---|
| Example 37 | 20.2 | 7.7 |
| Example 39 | 18.8 | 7.5 |
| Example 40 | 17.1 | 7.3 |
| Example 41 | 18.2 | 7.2 |
| Example 42 | 17.6 | 7.5 |
| Example 43 | 17.6 | 7.5 |
| Example 44 | 18.0 | 7.6 |
| Example 45 | 18.5 | 7.7 |
| Example 46 | 18.6 | 7.5 |
| Example 47 | 18.4 | 7.4 |
| Example 48 | 17.3 | 7.7 |
| Example 49 | 17.1 | 8.0 |
| Example 50 | 15.6 | — |
| Example 51 | — | 6.9 |

Evaluation of Hair Volume and Frizz

Hair volume was measured by digital image analysis using ImageJ software. Hair swatches were mounted on a holder in front of a light box, images were taken and evaluated. For each measurement, nine images were used, and the swatch area corresponding to the continuous dark signal intensity was measured. Volume increase or reduction was compared to that of an untreated hair swatch. The frizz component of hair volume was calculated with the ImageJ software as the area in the image on the perimeter of the continuous hair swatch, in which single fibres were visible. The results are reported as volume or frizz change in % of the volume/frizz of the untreated hair (increase—positive; reduction—negative).

The following formulations were tested:

TABLE 6

| Ingredient | Example 68 | Example 69 | CE 1 | CE 3 |
|---|---|---|---|---|
| Cetearyl Alcohol | 4.0 | 4.0 | 4.0 | 4.0 |
| Example 5 | 1.7 | 1.7 | — | — |
| CTAC | 0.3 | 0.3 | 2.0 | 2.0 |
| Xiameter PMX-200 | 0.2 | — | 0.2 | — |
| Preservative | q.s. | q.s. | q.s. | q.s. |
| Water | Ad. 100 | Ad. 100 | Ad. 100 | Ad. 100 |

TABLE 7

Hair volume changes, virgin European hair:

| Product tested | CE 3 | CE 1 | Example 69 | Example 68 |
|---|---|---|---|---|
| Volume change, % | +11.3 | +4.2 | +10.1 | −2.1 |

It is clear and consistent with the knowledge in the field that hair cosmetics without silicone increase hair volume (CE 3 and Example 69). To the contrary, products with silicone reduce hair volume to give the effect of smooth and sleek hair. Volume reduction by using the product with Example 5 is stronger than for a conventional conditioner (CE 1).

TABLE 8

Hair frizz changes, virgin European hair:

| Product tested | CE 1 | Example 69 | Example 68 |
|---|---|---|---|
| Frizz change, % | −33 | −49.3 | −84.5 |

Hair frizz is a component of hair volume, and is generally unwelcome among consumers, as it decreases hair gloss and makes hair less manageable. Typical conditioners are able to reduce hair frizz, and those with added silicone normally have a stronger effect. Material of Example 5 reduces hair frizz stronger than a benchmark conditioner CE 1 (with silicone). Whether silicone-free or with silicone, Example 5 has a much stronger effect in frizz reduction, and can be used in smoothing, frizz reducing products. Hair gloss of frizz-free hair is also expected to be higher.

Evaluation of Hair Smoothness and Repair

Hair smoothness and repair was measured on various types of hair using Diastron (UK) MTT 175 tester with the friction accessory. Friction coefficient for hair when moved in the root-to-tip direction under external weight is interpreted as smoothness, and in the opposite direction (tip-to-root) as hair repair.

The following formulations were tested:

TABLE 9

| Ingredient | Example 68 | CE 1 | CE 2 |
|---|---|---|---|
| Cetearyl Alcohol | 4.0 | 4.0 | 4.0 |
| Example 5 | 1.7 | — | — |
| CTAC | 0.3 | 2.0 | — |
| BTAC | — | — | 2.0 |
| Xiameter PMX-200 | 0.2 | 0.2 | 0.2 |
| Preservative | q.s. | q.s. | q.s. |
| Water | Ad. 100 | Ad. 100 | Ad. 100 |

Hair Smoothness

The measurement error is +/−2%. The following results were obtained for friction coefficient for European (virgin and 4 h bleached) and Asian (virgin) hair:

TABLE 10

| Product tested | CE 1 | CE 2 | Example 68 |
|---|---|---|---|
| Friction coefficient root-to-tip - EU virgin | 0.5838 | 0.5462 | 0.5378 |
| Friction coefficient root-to-tip - EU bleached | — | 0.5728 | 0.5458 |
| Friction coefficient root-to-tip - Asian virgin | 0.5856 | — | 0.5650 |

A lower friction coefficient corresponds to smoother hair, and differences of 0.01 are already significant. The conditioner of Example 68 shows improved performance on that benefit in comparison with typical conditioners (CTAC and BTAC).

Hair Repair

The measurement error is +/− 2%. The following results were obtained for return friction coefficient for European (virgin and 4 h bleached) and Asian (virgin) hair:

TABLE 11

| Product tested | CE 1 | CE 2 | Example 68 |
|---|---|---|---|
| Friction coefficient tip-to-root - EU virgin | 1.217 | 1.202 | 1.031 |
| Friction coefficient tip-to-root - EU bleached | 1.120 | 1.077 | 1.070 |
| Friction coefficient tip-to-root - Asian virgin | 1.155 | — | 1.115 |

Material of Example 5, when formulated in a hair conditioner, shows a significantly improved benefit of hair repair in comparison with conventional conditioners (CE 1 and CE 2), on all hair types used for the test.

Evaluation of Hair Gloss/Shine with and without Silicone

Glossy hair is among the largest consumer needs when hair care products are considered. A number of commonly known hair glossers are used in the industry, most frequently silicones. However, with the silicone-free product segment increasing, and with more consumers perceiving silicones as environmentally unfriendly, it is important that a hair conditioner without silicone also provides a high level of hair gloss. Hair gloss on the dry swatches was measured with Samba Hair System (Bossa Nova Tech, CA, USA). BNT numbers for hair gloss calculated by the Bossa Nova algorithm are reported.

TABLE 12

| Product tested | CE 1 | CE 3 | Example 68 | Example 69 |
|---|---|---|---|---|
| EU virgin hair | 15.9 | — | 17.0 | 16.9 |
| EU bleached hair | 6.6 | 6.5 | 7.0 | 7.2 |

Conditioner examples 68 (with silicone) and 69 (silicone-free), both containing the material of Example 5, provide higher shine than a prior-art formulations with cetrimonium chloride.

Analytics

The molecular mass Mn (number average) aka number average molecule weight used herein is measured by GPC. GPC is a special type of liquid chromatography in which the sample is separated according to the hydrodynamic volumes of the individual constituents. Detection is effected by e.g. refractive index and yields a simple distribution curve. To attribute actual molecular weight values to the curve, it is necessary to calibrate the column by passing down polymers of known molecular weight. GPC herein was determined under the following conditions:

Column: 1×PSS SDV Guard, 5 micron, 50 mm×8.0 mm ID
1×PSS SDV 100 Angstroms, 5 micron, 300 mm×8.0 mm ID
1×PSS SDV 1000 Angstroms, 5 micron, 300 mm×8.0 mm ID
1×PSS SDV 100000 Angstroms, 5 micron, 300 mm×8.0 mm ID
Detector: RID (refractive index detector)
Oven temperature: 40° C.
Flow: 1 ml/min
Injection volume: 50 µl
Eluent: THF
Calibration method: Conventional
Standards: Polyethylene glycol standards in the range from 430 to 44700 Dalton Internal Standard: Toluene.

The invention claimed is:

1. A cosmetic composition, comprising at least one oligoester ammonium salt (OAS) and at least one cosmetically acceptable component (F), whereby the at least one oligoester ammonium salt (OAS) is prepared by a process comprising the steps of:
(i) heating a mixture of components (a) to (d) while continuously removing reaction water:
0.5 to 3.0 molar equivalents of a diethanolamine compound according to formula (a)

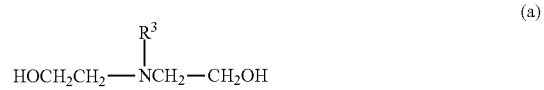

wherein $R^3$ is a linear or branched $C_1$-$C_6$-alkyl;
0.5 to 1.5 molar equivalents of a dicarboxylic acid according to formula (b)

wherein $R^2$ is a linear or branched $C_1$-$C_{10}$-alkylene or a linear or branched $C_2$-$C_{10}$-alkenylene;
0.5 to 1.5 molar equivalents of an organic triol according to formula (c2)

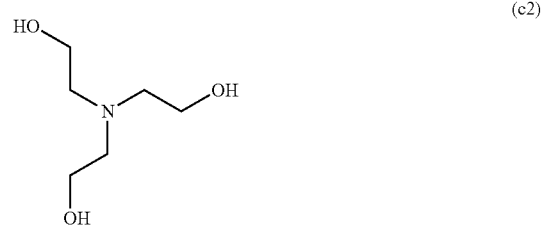

1.0 molar equivalent of a monocarboxylic acid according to formula (d)

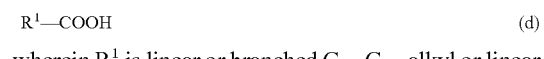

wherein $R^1$ is linear or branched $C_{20}$-$C_{24}$-alkyl or linear or branched $C_{20}$-$C_{24}$-alkenyl;
to form an oligoester product;
(ii) reacting the oligoester product of step (i) with a quaternization agent (e);
to form the oligoester ammonium salt (OAS) and (iii) optionally removing and purifying the at least one oligoester ammonium salt (OAS).

2. The cosmetic composition comprising at least one oligoester ammonium salt (OAS) according to claim 1, in which in the diethanolamine component (a), $R^3$ is methyl.

3. The cosmetic composition comprising at least one oligoester ammonium salt (OAS) according to claim 1, in which the dicarboxylic acid (b) is selected from the group consisting of adipic acid, glutaric acid, succinic acid, sebacid acid, itaconic acid, maleic acid, and combinations thereof.

4. The cosmetic composition comprising at least one oligoester ammonium salt (OAS) according to claim 1, in which the carboxylic acid (d) comprises or is behenic acid.

5. The cosmetic composition comprising at least one oligoester ammonium salt (OAS) according to claim 1, in which the components (a), (b), (c2) and (d) are used in the following molar ratios: from 0.75-3.0, from 0.5-1.5, from 0.5-1.5, and 1, respectively.

6. The cosmetic composition comprising at least one oligoester ammonium salt (OAS) according to claim 1, prepared by first heating the mixture of components (a), (b), (c2) and (d) in step (i) to a temperature from 80 to 220° C., and in step (ii) subsequent reaction of the obtained oligoester product with a quarternization agent (e).

7. The cosmetic composition comprising at least one oligoester ammonium salt (OAS) according to claim 1, in which the oligoester ammonium salt (OAS) has a molecular mass Mn (number average) of from 600 to 4000 g/mol.

8. The cosmetic composition according to claim 1, comprising 0.01 to 20% by weight of one or more oligoester ammonium salts (OAS) and further comprising at least 0.5% by weight of one or more further components (F), wherein the one or more further components (F) is selected from the group consisting of acidity regulators, glossers, lubricants, and further surfactants.

9. A method of preparing a cosmetic composition, according to claim 1, comprising the step of preparing one or more oligoester ammonium salts (OAS) and mixing the OAS with one or more further components (F).

10. A method of treating hair, wherein the cosmetic composition according to claim 1 is a hair conditioner composition, comprising:
   a) applying the hair conditioner composition onto wet hair and then
   b) removing the conditioner composition from the hair.

11. The method according to claim 10, comprising:
   (a) applying a shampoo composition onto the hair; and then
   (b) washing the hair with the shampoo composition; and then
   (c) removing the shampoo composition from the hair; and then
   (d) applying the hair conditioner composition onto wet hair, and then removing the conditioner composition from the hair.

* * * * *